United States Patent
Iatrou et al.

(10) Patent No.: US 7,031,426 B2
(45) Date of Patent: Apr. 18, 2006

(54) METHODS AND SYSTEM FOR DETECTING COMPONENTS OF PLAQUE

(75) Inventors: Maria Iatrou, Clifton Park, NY (US); Ricardo Scott Avila, Clifton Park, NY (US); Peter Michael Edic, Albany, NY (US); Jiang Hsieh, Brookfield, WI (US); James Walter LeBlanc, Niskayuna, NY (US); Xiaoye Wu, Rexford, NY (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 51 days.

(21) Appl. No.: 10/625,437

(22) Filed: Jul. 23, 2003

(65) Prior Publication Data
US 2004/0136491 A1   Jul. 15, 2004

Related U.S. Application Data

(60) Provisional application No. 60/398,341, filed on Jul. 23, 2002.

(51) Int. Cl.
*A61B 6/03* (2006.01)
(52) U.S. Cl. ............................................ 378/5; 378/18
(58) Field of Classification Search .................... 378/4, 378/5, 18, 207
See application file for complete search history.

(56) References Cited

U.S. PATENT DOCUMENTS

| | | | |
|---|---|---|---|
| 4,571,491 A * | 2/1986 | Vinegar et al. ............. 378/207 |
| 5,115,394 A * | 5/1992 | Walters ....................... 382/131 |
| 5,122,664 A * | 6/1992 | Ito et al. ...................... 378/207 |
| 5,218,533 A * | 6/1993 | Schanen ......................... 378/9 |
| 5,335,260 A * | 8/1994 | Arnold ........................ 378/207 |
| 5,396,530 A * | 3/1995 | Tsutsui et al. ............ 378/98.11 |
| 5,668,846 A * | 9/1997 | Fox et al. ........................ 378/4 |
| 5,867,553 A   | 2/1999 | Gordon et al. |
| 6,001,054 A * | 12/1999 | Regulla et al. ................. 600/1 |
| 6,028,909 A * | 2/2000 | Zmora .......................... 378/15 |
| 6,094,467 A * | 7/2000 | Gayer et al. .................... 378/4 |
| 6,148,057 A * | 11/2000 | Urchuk et al. ............... 378/207 |
| 6,233,304 B1  | 5/2001 | Hu et al. |
| 6,574,302 B1* | 6/2003 | Adriaansz .................... 378/207 |
| 6,816,564 B1* | 11/2004 | Charles et al. .................. 378/5 |
| 2001/0018042 A1* | 8/2001 | Teirstein et al. .............. 424/9.1 |
| 2002/0131544 A1* | 9/2002 | Aradate et al. ................. 378/4 |
| 2003/0060877 A1* | 3/2003 | Falotico et al. ............ 623/1.42 |
| 2003/0095693 A1* | 5/2003 | Kaufman et al. ........... 382/128 |

FOREIGN PATENT DOCUMENTS

| EP | 1087339 A1 * | 3/2001 |
| WO | WO 94 12855 A | 6/1994 |
| WO | WO 0033252 A | 6/2000 |

OTHER PUBLICATIONS

Arfelli, Fulvia, "Synchrotron light and imaging systems for medical radiology", Nuclear Instruments and Methods in Physics Research, Section A, vol. 454, Nov. 25, 2000, pps. 11-25.*

(Continued)

*Primary Examiner*—Edward J. Glick
*Assistant Examiner*—Chih-Cheng Glen Kao
(74) *Attorney, Agent, or Firm*—Carl B. Horton, Esq.; Armstrong Teasdale LLP (57) ABSTRACT

A method including detecting components of plaque using a multi-energy computed tomography (MECT) system is provided.

25 Claims, 6 Drawing Sheets

OTHER PUBLICATIONS

Lazos et al., "A Software Data Generator for Radiographic Imaging Investigations", IEEE Transactions on Information Technology in Biomedicine, vol. 4, No. 1, Mar. 2000, pps. 76-79.*

Xiaoye Wu, "Method and Apparatus for Generating a Density Map Using Duel-Energy CT", U.S. Appl. No. 10/624,417 filed Jul. 22, 2003, 25 pages, Drawings 4 pgs.

Peter Edic, "Apparatuses, Methods, and Algorithms for Using Imaging Date to Enable Reconstruciton of Dynamic Structures", U.S. Provisional Appl. No. 60/397,658, (41 pgs), Attachment A (33 pgs), Attachment B (7 pgs), Attachment C (3 pgs.), Attachment D (3 pgs), Attachment E (1 pg), Attachment F (37 pgs) and Attachment G (28 pgs).

International Search Report, International Appl. No. PCT/US03/22861, Classification of Subject Matter: IPC 7, A61b6/03, Search completion date: Oct. 15, 2003, 4 pages.

* cited by examiner

METHODS AND SYSTEM FOR DETECTING COMPONENTS OF PLAQUE

CROSS REFERENCE TO RELATED APPLICATIONS

This application claims the priority of U.S. Provisional Patent Application Ser. No. 60/398,341 filed Jul. 23, 2002, which is hereby incorporated by referenced in its entirety.

BACKGROUND OF THE INVENTION

This invention relates to imaging systems, and more particularly to methods and systems for detecting components of plaque.

Recent advancements in computed tomography (CT) technology have resulted in faster scanning speeds, larger coverage with multiple detector rows, and thinner slices. However, energy resolution in measurements obtained with these systems is still a missing piece. The wide x-ray photon energy spectrum output from the x-ray source and the lack of energy resolution from CT detection systems preclude energy discrimination CT.

The X-ray attenuation through a given object is strongly dependent on the incident x-ray photon energy. This physical phenomenon manifests itself in an image as beam-hardening artifacts, such as, non-uniformity, shading, and streaks. Some beam-hardening artifacts can be easily corrected, but other beam-hardening artifacts may be more difficult to correct. In general, known methods to correct beam hardening artifacts include water calibration, which includes calibrating each CT machine to remove beam hardening from materials similar to water, and iterative bone correction, wherein bones are separated in a first-pass image reconstruction then the measurements are corrected for the beam hardening resulting from the bones in a second-pass reconstruction. However, beam hardening from materials other than water and bone, such as metals and contrast agents, may be difficult to correct without added processing of the measured data. In addition, even with the above described correction methods, conventional CT does not provide quantitative image values. Rather, the same material at different locations within the image often shows a different CT number.

Another drawback of conventional CT is the reduced level of material characterization. For example, a highly attenuating material with a low density can result in the same CT number in the image as a less attenuating material with a high density. Thus, there is little or no information about the material composition of a scanned object based solely on the CT number.

BRIEF DESCRIPTION OF THE INVENTION

In one aspect, a method is provided. The method includes detecting components of plaque using a multi-energy computed tomography (MECT) system.

In another aspect, a method for detecting components of plaque is provided. The method includes generating information regarding projection data of phantoms by using an MECT system, and obtaining the components of the plaque from the information.

In yet another aspect, an MECT system is provided. The MECT system includes at least one radiation source configured to transmit x-rays that intersect an object; at least one detector configured to detect the x-rays; a controller coupled to the detector; and a computer configured to instruct the MECT system to detect components of plaque.

In still another aspect, a computer readable medium encoded with a program is provided. The program is configured to instruct a computer to detect components of plaque within an object that is scanned using a multi-energy tomography (MECT) system.

In still another aspect, a computer encoded with a program is provided. The program is configured to instruct an MECT system to detect components of plaque within an object that is scanned using the MECT system.

DETAILED DESCRIPTION OF THE INVENTION

It is believed that progression of arteriosclerosis causes a build-up of fat-laden deposits on vessel walls, causing progressive narrowing in the vessel, such as in a carotid or a coronary artery. Eventually, lumen or blood flow within the vessel is reduced to such a level that a tissue, such as, a heart muscle or brain tissue, is starved of oxygen-carrying blood and the tissue dies, resulting in a heart attack or stroke. Comparatively, in atherosclerosis, a majority of patients with acute cardiac disease exhibit an inflammatory process within the vessel wall itself. Low-density lipoproteins (LDLs) accumulate in the vessel wall and attract immune system cells into the vessel wall as well. The immune system cells ingest the modified LDLs, giving rise to fatty droplets, which constitute a lipid core of a plaque. The inflammatory cells promote growth of the plaque and development of a fibrous cap composed of collagen fibers formed by smooth muscle cells over the lipid core. When the inflammatory cells flare, immune system cells secrete enzymes that degrade collagen and prevent the development of new collagen fibers to repair cap damage. The weakening of the cap may continue until a fissure occurs and the blood of the lumen intermingles with the lipid core, rich in proteins that foster blood coagulation. As a result, a clot forms and the vessel may be occluded, resulting in an ischemic event. If the clot is not occlusive, scar tissue develops and the plaque is enlarged, giving rise to a chronic condition.

In coronary atherosclerosis, thrombi, as well as calcified, intermediate, and soft plaques could be present. Plaque composition is believed to be indicative of the risk of acute coronary syndromes. Soft plaque includes a high lipid concentration, a fibrous thin cap and inflammatory cells. Intermediate plaques include fibrous tissue, lower concentrations of lipids and inflammatory cells. Calcified plaques include a high concentration of calcium. If soft plaque is present, there may be an increased risk of a stroke or a heart attack. It is believed that thrombi have a density less than 20 Hounsfield units (HU), soft plaques have a density less than 50 HU, intermediate plaques have a density between 50 and 120 HU, and calcified plaques have a density over 120 HU. Hounsfield units, also known as CT numbers, are used to control the brightness of a corresponding pixel on a cathode ray tube display and reflect the consistency of the different types of plaques. However, it is challenging to identify and discriminate plaques with low or no concentration of calcium.

In some CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of processed x-ray attenuation measurements, i.e. projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional (2D) slice taken through the object. One method for reconstructing an image from a set of projection data is referred to in the art as the filtered back projection technique. This process converts the attenuation measurements from a scan into integers called Hounsfield units.

To reduce the total scan time, a "helical" scan may be performed. To perform a "helical" scan, the object is moved into the scanner while the data for the prescribed number of slices is acquired. Such a system generates a single helix from an x-ray fan beam helical scan. The helix mapped out by the x-ray fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The helical weighting algorithms also scale the data according to a scaling factor, which is a function of the distance between the x-ray source and the object. The weighted and scaled data is then processed to generate CT numbers and to construct an image that corresponds to a 2D slice taken through the object.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
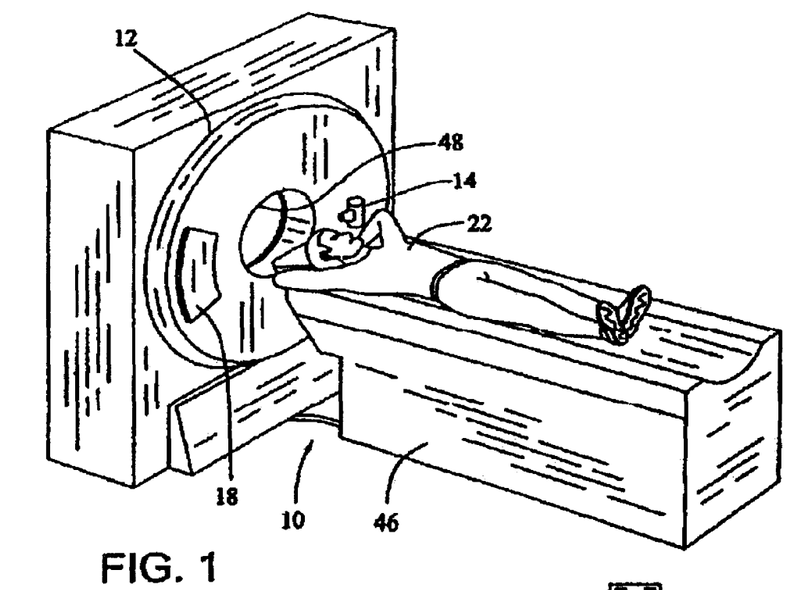
FIG. 1 is a pictorial view of a multi-energy computed tomography (MECT) imaging system in which a method for detecting components of plaque is implemented.
Figure 2:
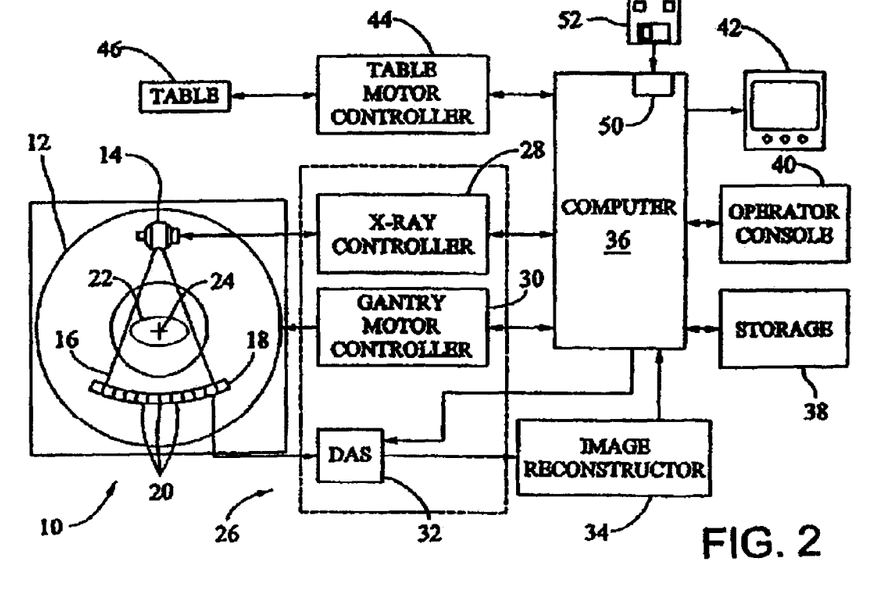
FIG. 2 is a block schematic diagram of the MECT system illustrated in FIG. 1.

Referring to FIGS. 1 and 2, a Multi-Energy multi-slice scanning imaging system, for example, a Multi-Energy computed tomography (MECT) imaging system 10, is shown as including a gantry 12 representative of a "third generation" CT imaging system. Methods for detecting components of plaque are implemented using MECT system 10. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence can be used to estimate the attenuation of the beam as it passes through patient 22. During a scan to acquire x-ray projection data, the components mounted on circular portion of gantry 12 therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan. Moreover, detector array 18 may be an area detector facilitating large imaging coverage on the patient 22 for each rotation of the circular portion of gantry 12.

Rotation of components in gantry 12 and the operation of x-ray source 14 are governed by a control mechanism 26 of MECT system 10. Control mechanism 26 includes an x-ray controller 28 that provides power and timing signals to x-ray source 14 and a gantry motor controller 30 that controls the rotational speed and position of components in gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to controllers, processors, microcontrollers, microcomputers, programmable logic controllers, application specific integrated circuits, and other programmable circuits, and these terms are used interchangeably herein. MECT system 10 is an energy-discriminating computed tomography (EDCT) system in that MECT system 10 is configured to be responsive to different incident x-ray spectra. This can be accomplished with a conventional third generation CT system by acquiring projection data sequentially using different x-ray tube voltages. For example, two scans are acquired either back to back or interleaved in which the tube operates at 80 kVp and 160 kVp potentials, for example, generating a low and high energy spectrum respectively. Alternatively, special filters are placed between x-ray source 14 and detector array 18 such that different detector rows collect projections of different x-ray energy spectrum. Yet another embodiment is to use energy sensitive detectors such that each x-ray photon reaching the detector is recorded with its photon energy. Although the specific embodiment mentioned above refers to a third generation CT system, the methods described herein equally apply to fourth generation CT systems (stationary detector—rotating x-ray source) and fifth generation CT systems (stationary detector and x-ray source), as well as other higher generation CT systems.

EDCT can lessen or eliminate the problems, such as lack of energy discrimination or material characterization, associated with some CT systems altogether. In the absence of object scatter, MECT system 10 may be used to separately detect two regions of the incident photon energy spectrum, the low-energy and the high-energy portions of the incident x-ray spectrum. The behavior at any other energy can be derived based on the signal from the two energy regions. This phenomenon is driven by the fundamental fact that in the energy region where medical CT is interested, two physical processes dominate the x-ray attenuation (1) Compton scatter and (2) the Photoelectric effect. In order to characterize the behavior of an object causing attenuation of the x-ray beam, two independent parameters are measured. Thus, detected signals from the two energy regions provide sufficient information to resolve the energy dependence of the object being imaged; hence, the composition of the material can be characterized.

The data analysis used in EDCT includes Compton and photoelectric decomposition and/or Basis material decomposition (BMD). In Compton and photoelectric decomposition, a pair of images is generated with MECT 10, which separately present the attenuation from the Compton and photoelectric processes—instead of obtaining one image characterizing the overall attenuation coefficient in the reconstructed CT image. Also, a slight modification in the processing allows the generation of images representing density and effective atomic number. The BMD method is based on the concept that the x-ray attenuation of any given material in the energy range for MECT can be represented by assuming a density mixture of other two known materials. These two materials are called the Basis Materials. Using BMD, two reconstructed images are obtained, each image representing the equivalent density of one of the basis materials. Since density is independent of x-ray photon energy, these images are relatively free of beam hardening artifacts. Additionally, the basis material is chosen to target a material of interest, thus enhancing the image contrast.

It should be noted that in order to optimize a multi-energy CT system not implementing energy discrimination with photon counting, the larger the energy separation in the x-ray spectra, the better the image quality. Also, the photon statistics in these two energy regions should be comparable, otherwise the energy region with reduced statistical information will dominate the noise in the reconstructed image.

There are different methods to obtain dual energy measurements: (1) scan with two distinctive energy spectra, (2) detect photon energy according to penetration depth at the detector, or (3) photon-counting with energy discrimination. Photon counting provides clean spectra separation and an adjustable energy separation threshold for balancing photon statistics.

FIGS. 3, 4, 5, and 6 illustrate a flowchart of an embodiment of a method for detecting components of a plaque, such as atherosclerotic plaque. The method is executed by computer 36 upon receiving images reconstructed by image reconstructor 34. The method includes detecting 66 components of a plaque, such as calcium, lipid, and smooth muscle cells, developed in patient 22 and includes quantification 68 of the components of plaque. MECT system 10 is used to detect the components. The components are detected by generating information regarding densities of constituent components of the plaque and characterizing the components of the plaque from the information. The information may be generated by simulating the data collection of projection data obtained with an object, such as, for instance, a phantom, to allow generation of reconstructed images of the phantom by MECT system 10. Material decomposition basis materials, such as water and iodine, of the phantom are assumed. The phantom includes regions with known material properties and known densities of water and iodine. For instance, the phantom includes a region with an iodine solution of known concentration, and thus known water and iodine densities. As another example, the phantom includes a region with an iodine solution of a different known concentration.

Figure 3:
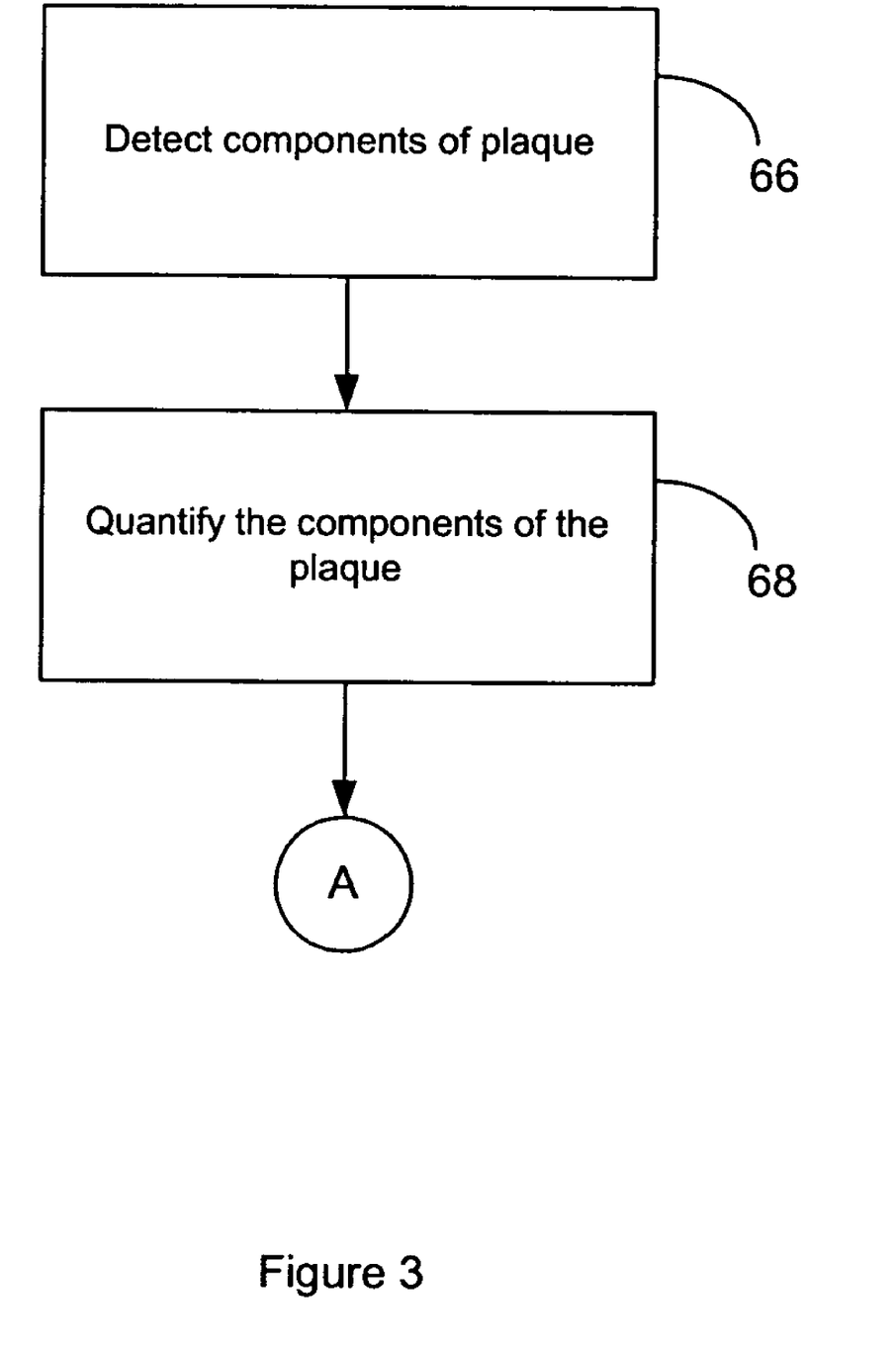
FIGS. 3, 4, 5, and 6 illustrate a flowchart of an embodiment of the method for detecting components of plaque.
Figure 4:
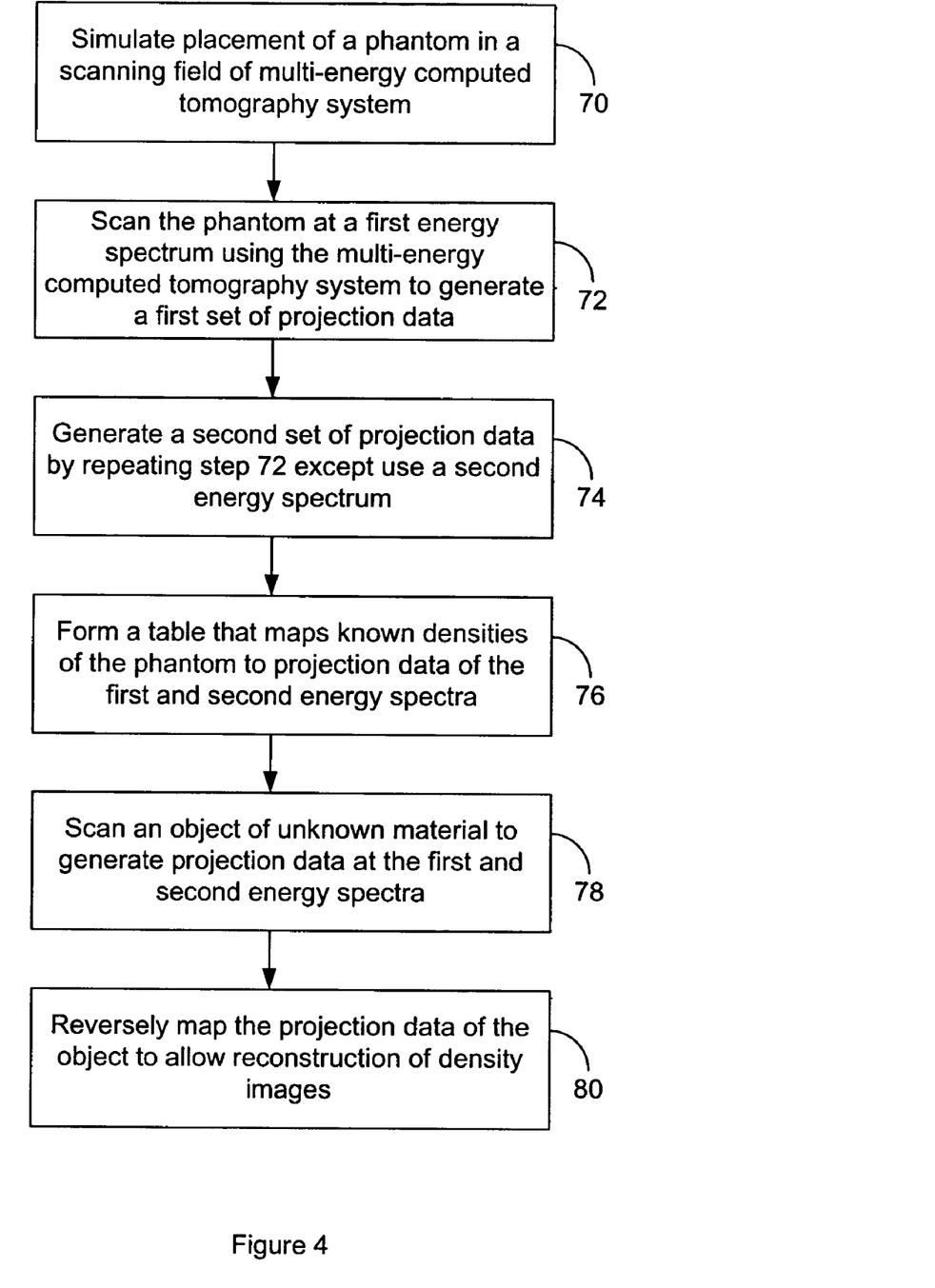

To generate the information, a first and the second sets of projection data are generated by spanning the entire space of iodine and water concentrations of interest within the phantom. The first set of projection data is generated by performing 70 a simulation of placing the phantom in a scanning field of MECT system 10 and scanning 72 the phantom at a first energy spectrum using MECT system 10. As an example, the first energy spectrum is a high or a low energy spectrum. Therefore, for known water and iodine densities, for a known material, projection data that correspond to the first energy spectrum are obtained. The second set of projection data of the phantom is obtained 74 in a similar manner as obtaining the first set of projection data except that the second set of projection data is generated by simulating the scanning of the phantom with a second energy spectrum. The second energy spectrum is a low energy spectrum if the first energy spectrum is a high-energy spectrum. Conversely, the second energy spectrum is a high-energy spectrum if the first energy spectrum is a low-energy spectrum. Once the simulated data acquisition is completed for the first and second energy spectrum scans, for all the known different iodine concentrations, a specific material basis decomposition look-up table is formed 76. If iodine concentrations are used, the look-up table maps known projection data generated from measurements of water and iodine in the phantom to allow generation of density distributions in first and second sets of images, where the first set of images is generated from the first set of projection data and the second set of images is generated from the second set of projection data. After the construction of the look-up table, the components of the plaque are obtained by scanning 78 an object, such as patient 22, of unknown material to generate projection data and using 80 the look-up table to allow generation of images of the density of the basis materials. As an example, the look-up table is reversely mapped to obtain material distributions within patient 22 from densities of material distributions within the phantom.

A detailed description of the step of using the look-up table to allow generation of images of the density of the basis materials has been described in an application titled "Method and Apparatus For Generating a Density Map Using Dual-Energy CT", having Ser. No. 10/624,417, and filed on Jul. 22, 2003, which is incorporated by reference herein in its entirety. The detailed description of the step of using the look-up table to allow generation of images of the density of the basis materials has also been described in a provisional application having Ser. No. 60/397,658 and filed on Jul. 23, 2002, which is also incorporated by reference herein in its entirety.

The components of the plaque are obtained by placing patient 22 in the scanning field of MECT system 10 and scanning patient 22 at the first and second energy spectrums using MECT system 10 to obtain reconstructions of the density of the basis materials within patient 22. In an alternative embodiment, the method includes scanning a first small cross section of patient 22. The first small cross section includes cells or elements that exist in a lipid core of the plaque but do not exist in the smooth muscles of the plaque. In yet another alternative embodiment, the method includes scanning a second small cross section of patient 22. The second small cross section includes the plaque. It is noted that additional energy levels can be used to scan the phantom or the object to generate the look-up table.

The method further includes quantifying 68 the components of the plaque. The method quantifies the components of the plaque by calculating composition density distributions, such as lipid burden or calcium burden, of the plaque and calculating total plaque burden. As an example, the total plaque burden is calculated by a thresholding method. The thresholding method distinguishes pixels that have a density greater than a number y. The pixels are pixels of images obtained by using MECT system 10. The total plaque burden in an organ of patient 22 is a weighted sum of densities greater than y of pixels of an image of the organ. The composition density distributions are calculated by a method similar to that used to calculate the total plaque burden. For instance, the lipid burden is calculated by distinguishing pixels of images obtained using MECT system 10 that have a density greater than a number v. The total lipid burden in an organ of patient 22 is a weighted sum of densities greater than v of pixels of an image of the organ. In an alternative embodiment, the quantities of the components are combined with measurements of geometry of lumen of patient 22 to assess degree and severity of stenosis. Other techniques for quantifying components of plaque are described in "Coronary Artery Calcium: Accuracy and Reproducibility of Measurements with Multi-Detector Row CT-Assessment of Effects of Different Thresholds and Quantification Methods 1," Cheng Hong, Kyongtae T. Bae and Thomas K. Pilgram, Radiology 2003, 227: 795–801; "Noninvasive quantification of coronary artery calcification: Methods and prognostic value," Sandra S. Halliburton, Arthur E. Stillman, Richard D. White, Cleveland Clinic Journal Of Medicine Volume 69, Supplement; and in "CT and MR for coronary Angiography & plaque imaging," Fayad et al., Circulation, October 2002, pp. 2026–2033.

The method also includes instructing 104 MECT system 10 to perform additional scans of patient 22 at different times and repeating step 66 shown in FIG. 3 each time a scan is performed. The method includes waiting 106 for a user to administer a contrast agent, such as non-ionic Iodine, Gadolinium, a blood pool contrast agent, and/or a contrast agent that adheres to specific molecules. The contrast agent is administered to accentuate the contrast in at least one of lipid-avid agents, plaque specific antigens, and/or plaque cells of patient 22. The method further includes repeating 107 step 66.

The method also includes waiting 108 for the user to administer a temperature-sensitive contrast agent to accentuate an inflamed plaque. Examples of the temperature-sensitive contrast agents include agents containing a lanthanide metal, such as Ce, Pr, Nd, Sm, Eu, Gd, Db, Dy, Ho, Er, Tm, and Yb. The method includes repeating 109 step 66.

Figure 5:
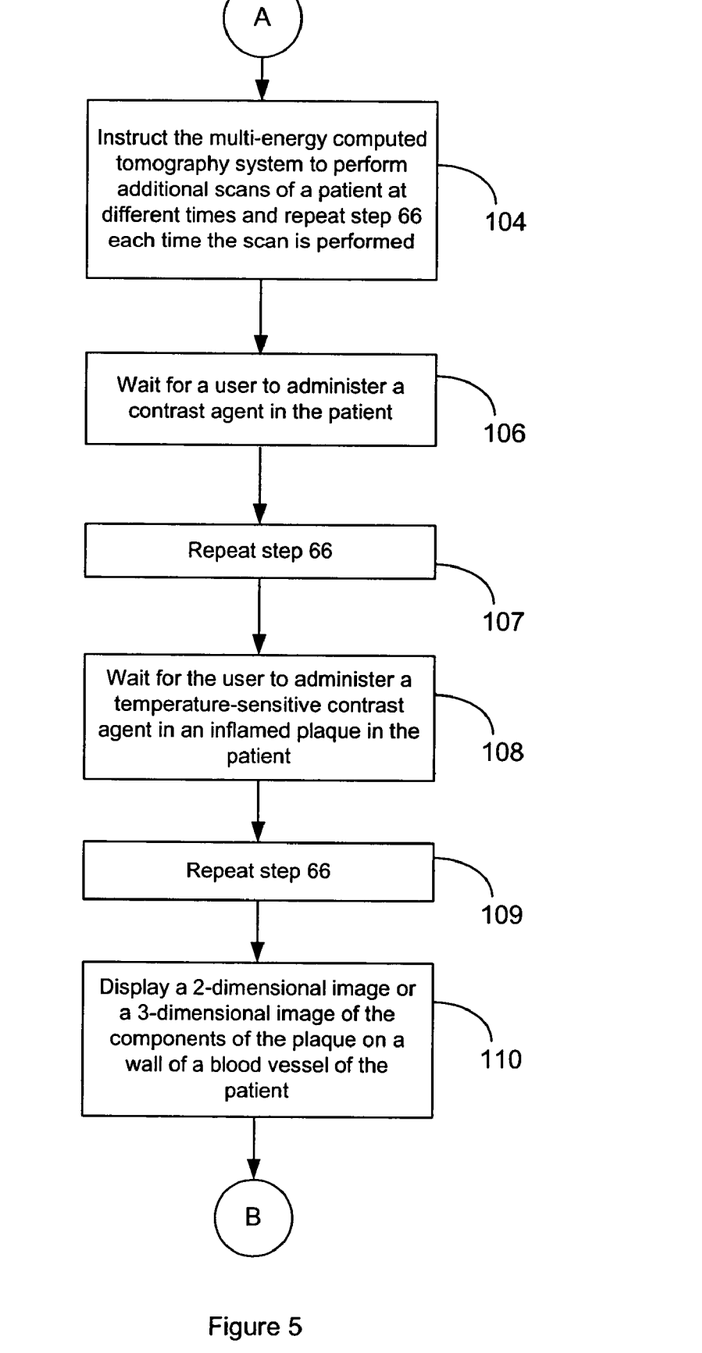
Figure 6:
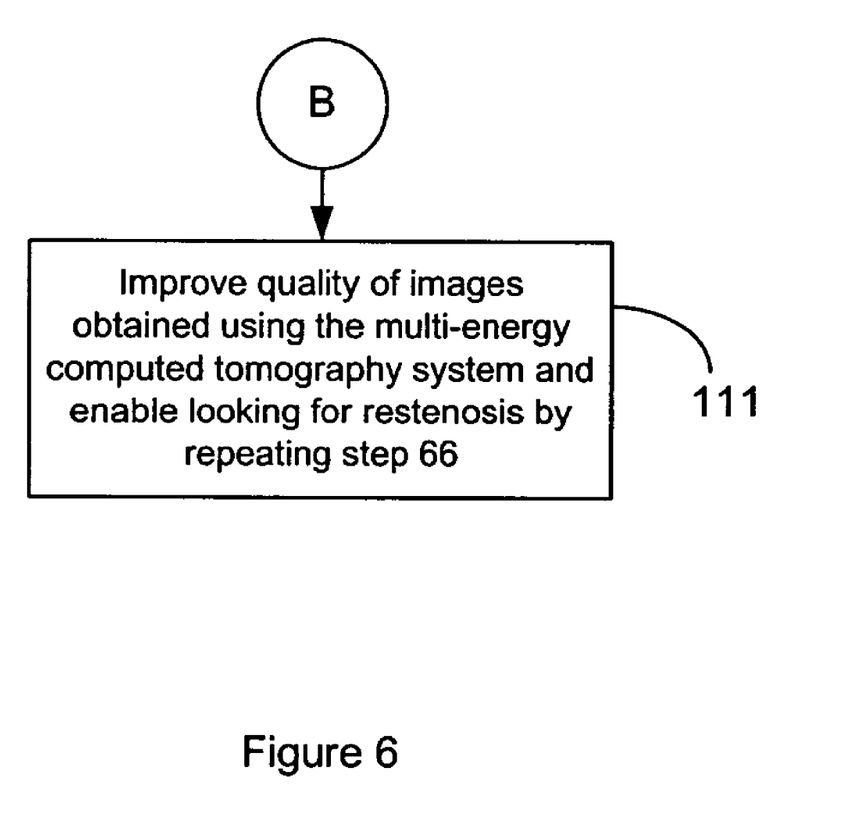

As identified in FIG. 5, the method further includes displaying 110 at least one of a 2-dimensional (2D) and a 3-dimensional (3D) image of the components of the plaque on a wall of an organ, such as an intestine or blood vessel of patient 22, and enabling viewing, from a viewpoint, a volume of the plaque in the 3D image. The method performs volume rendering for viewing the 3D image or using visualization methods to traverse through the 3D image from at least one viewpoint. Volume rendering is a technique used for visualizing sampled functions in three spatial dimensions. Volume rendering is applied to medical imaging where volume data is available from MECT system 10. Image reconstructor 34 produces three-dimensional stacks of parallel plane images, or slices, each of which consist of an array of material densities. Some CT images have a resolution of 512×512×12 bits, and include up to 500 slices in a stack. In a 2D domain, slices can be viewed one at a time. An advantage of CT images obtained from image reconstructor 34 is that each slice only contains information from one plane. The availability of the stacks of parallel data produced by MECT system 10 prompted the development of techniques for viewing the volume data as a three-dimensional field, rather than as individual slices. Therefore, the volume data can now be viewed from any viewpoint.

The method includes repeating 111 step 66 after a patient with metal stents and/or metal valves is scanned. Repeating 111 step 66 removes beam-hardening artifacts. The beam-hardening artifacts are removed since MECT system 10 scans at multiple energies, as described above, to obtain the images of material densities within patient 22 including the stent. Moreover, repeating 111 step 66 enables looking for restenosis within the stent, which is an reappearance of plaque within the stent, by improving the quality of images obtained using MECT system 10. It is noted that instead of simulating a scan of the phantoms in step 70, an actual placement and an actual scan of the phantoms can be performed using MECT system 10. It is also noted that additional lists of materials and energies can be created by scanning phantoms with varying compositions of substances, such as, for instance, calcium, iodine, and water, at additional energies, such as, third and fourth energies. The additional lists can be added to the information in the look-up table.

It is noted that the steps of the flowcharts of FIGS. 3, 4, 5, and 6 can be executed in a different order than shown in the Figures. For example, steps 108 and 109 can be executed before step 106 and after step 104. As another example, steps 106 and 107 can be performed before step 110 and after step 109. Moreover, it is not necessary to execute all procedures identified in FIGS. 5 and 6 to obtain useful information.

Figure 7:
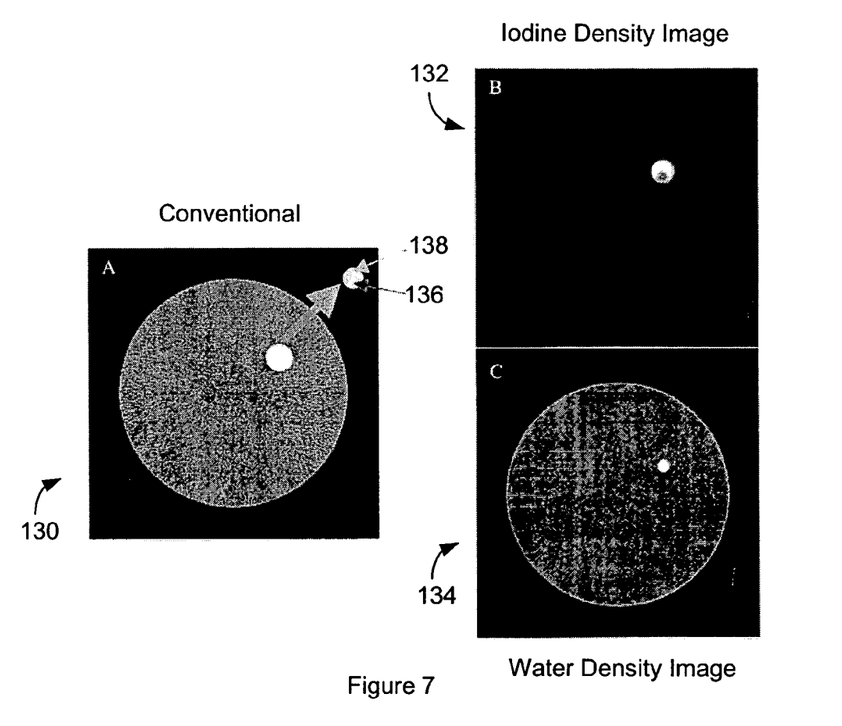
FIG. 7 illustrates a plurality of images.

FIG. 7 illustrates a plurality of images including image 130, image 132, and image 134. Image 130 is an image reconstructed using conventional CT imaging techniques. A high-density organ of image 130 includes calcium 136 and iodine 138 at densities that have reconstruct to the same effective CT number or Hounsfeld unit. Hence, there is no difference visible between calcium 136 and iodine 138 within image 130. Image 132 is an iodine density image where iodine 138 is used as a basis material and image 134 is a water density image, where water is used as a basis material. Images 132 and 134 were generated by implementing the method of FIGS. 3, 4, 5, and 6. Specifically, images 132 and 134 were obtained by implementing step 66, including the basis material decomposition steps of the method. The method enables discrimination of calcium 136, visible as a white area, and iodine 138, visible as a grey area in image 132. Calcium 136 and iodine 138 can be distinguished from each other since each has different attenuation characteristics as a function of x-ray spectral energy. Calcium 136 is evident in both images 132 and 134 because it is not one of the basis materials used for decomposition.

Figure 8:
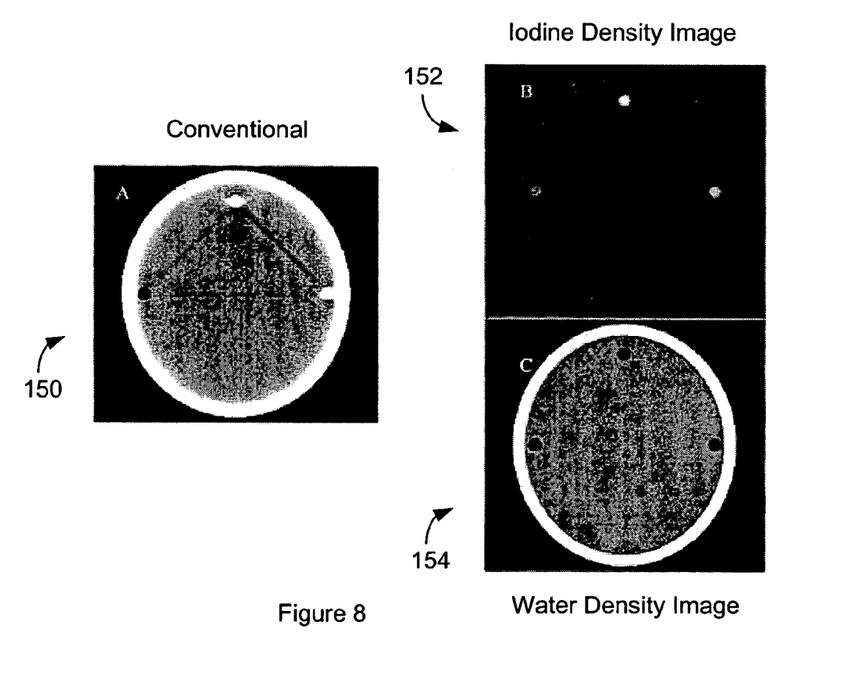
FIG. 8 illustrates another plurality of images.

FIG. 8 illustrates a plurality of images including image 150, image 152, and image 154. Image 150 is an image reconstructed using conventional CT imaging techniques. High-density organs within image 150 demonstrate beam-hardening artifacts, such as non-uniformity, shading and streaking, which occur in some CT images. Image 152 is an iodine density image where iodine 138 is used as a basis material and image 154 is a water density image, where water is used as a basis material. Images 152 and 154 were generated by implementing the method of FIGS. 3, 4, 5, and 6. Specifically, images 152 and 154 were obtained by implementing the basis material decomposition method in combination with step 66. Non-uniformity, shading, and streaking have been removed in images 152 and 154. The basis material decomposition method in combination with the above described implementation of step 66 results in images 152 and 154 which are free of beam hardening artifacts.

Hence, the herein described systems and methods for detecting components of plaque take into account system behavior such as detector response and detector signal pileup. The systems and methods have shown improved results as shown in FIGS. 7 and 8. Potential applications of the systems and methods include coronary artery imaging and calcium scoring using a protocol specifying contrast injection. Additional potential applications include elimination of beam-hardening artifacts in stents and thus improvement of image quality within stents, enabling assessment of in-stent restenosis and plaque characterization. Moreover, the systems and methods make possible continuous screening of high-risk patient populations that may be selected based on genetic or environmental history factors. The systems and methods also make possible automatic detection of high-risk vascular regions, denoted as unstable plaque regions, based on vascular geometry, which is of great benefit to a physician. The systems and methods make possible automatic detection of plaque burden and composition, which is also of benefit to the physician. The automatic detection allows for more thorough detection of disease, especially early disease markers, in large projection datasets and may permit automated quantification of disease at all vascular locations. Automated computation may also be employed to fully detect and characterize each plaque region into stages corresponding to different risk groups or intervention/therapy groups. The computations may then be highlighted during physician review and recommendations for a follow up period and scanning protocols may be made. Once cardiovascular disease (CVD) is detected, several methods may be employed to automatically detect and diagnose CVD including advanced pattern recognition methods, such as, neural networks and model-based algorithms. Progression and regression of CVD is also possible if multiple scans are performed by MECT system 10 at varying time points. The rate of progression of CVD can be measured in patient 22 and compared to normal populations, accounting for age, sex, and other biases. These comparisons will assist in identifying patient 22 that is at a high risk of CVD and permit the monitoring of therapy. Advanced pattern recognition methods may again be employed on data acquired using MECT system 10 and other patient data to ensure that an optimal therapy path is administered for patient 22.

The herein described systems and methods may also be used as an image-based surrogate for drug therapy clinical trials. This allows an assessment of the efficacy of pharmacological agents during early drug development and clinical trials. The systems and methods can be applied to diagnosis or treatment of a disease, such as CVD, by following the regression of the disease. The systems and methods can also be applied to stent imaging to assess the presence and extent of re-stenosis.

While the invention has been described in terms of various specific embodiments which require acquiring projection data at different x-ray spectra, it is possible to implement the scheme using only one acquisition if a photon counting MECT is employed where the energy of each detected photon is measured. A thresholding method is used in which photons having an energy level higher than a threshold are binned as one group and photons having an energy level lower than the threshold are binned as another group. In this case, an optimal threshold between the upper and lower energy levels is selected from the measurements to optimize distinguishing the densities of the basis materials.

While the invention has been described in terms of various specific embodiments, those skilled in the art will recognize that the invention can be practiced with modification within the spirit and scope of the claims.

What is claimed is:

1. A method comprising:
   detecting components of plaque using a multi-energy computed tomography (MECT) system, wherein said detecting the components of the plaque includes generating a look-up table by using at least one phantom; and
   quantifying the components of the plaque by determining a weighted sum of densities of pixels of an image of an organ including the plaque.

2. A method in accordance with claim 1 wherein the phantom includes a simulated phantom, said method comprising:
   obtaining the components of the plaque by using the generated look-up table, wherein said generating the look-up table includes producing the look-up table by using the simulated phantom, wherein the look-up table maps different densities of a selected basis material of the simulated phantom to projection data for different energy spectra.

3. A method in accordance with claim 2 wherein said generating the look-up table comprises:
   obtaining first and second sets of projection data of the simulated phantom with a set of known material properties by:
   placing the simulated phantom in a scanning field of the MECT system; and
   scanning the simulated phantom at first and second energy spectra using the MECT system.

4. A method in accordance with claim 3 wherein said obtaining the components of the plaque comprises:
placing an object in the scanning field of the MECT system;
scanning the object at the first and second energy spectra using the MECT system to obtain projection data of the object; and
enabling, utilizing the look-up table, a reconstruction of images of a distribution of densities of the object by reversely mapping the projection data of the object to densities of the selected basis material, wherein the selected basis material includes at least one of iodine and water.

5. A method in accordance with claim 1 wherein said generating the look-up table comprises:
obtaining projection data of the phantom with a set of known material properties by:
placing the phantom in a scanning field of the MECT system;
scanning the phantom using the MECT system;
counting photons generated from the scan; and
distinguishing the photons based on an energy threshold.

6. A method in accordance with claim 5 wherein said obtaining the components of the plaque comprises:
placing an object in the scanning field of the MECT system;
scanning the object using the MECT system to obtain projection data of the object; and
enabling, utilizing the look-up table, a reconstruction of images of a distribution of densities of the object by reversely mapping the projection data of the object to densities of the selected basis material, wherein the selected basis material includes at least one of iodine and water.

7. A method in accordance with claim 1 further comprising:
performing additional scans of an object at different times; and
repeating said detecting the components of the plaque.

8. A method in accordance with claim 1 further comprising:
administering a contrast agent in at least one of lipid-avid agents, plaque specific antigens, and plaque cells; and
repeating said detecting the components of the plaque.

9. A method in accordance with claim 1 further comprising:
administering a temperature-sensitive contrast agent in an inflamed plaque; and
repeating said detecting the components of the plaque.

10. A method in accordance with claim 1 wherein said quantifying the components of the plaque comprises:
calculating composition distributions of the plaque; and
calculating total plaque burden.

11. A method in accordance with claim 1 further comprising:
displaying at least one of a 2-dimensional (2D) and a 3-dimensional (3D) image of the components of the plaque on a wall of an organ of an object; and
viewing, from a viewpoint, a volume of the plaque in the 3D image.

12. A method in accordance with claim 1 further comprising:
improving quality of images of an object having at least one of metal stents and valves by removing beam-hardening artifacts in the images; and
enabling visualization of restenosis within at least one of the metal stents by repeating said detecting the components of plaque.

13. A method for detecting components of plaque comprising:
generating information regarding projection data of phantoms by using a multi-energy computed tomography (MECT) system;
generating a look-up table by using one of the phantoms;
obtaining the components of the plaque from the information; and
enabling visualization of restenosis within one of a metal stent and a metal valve by repeating said obtaining the components of plaque after scanning a patient having the one of the metal stent and the metal valve.

14. A multi-energy computed tomography (MECT) system comprising:
at least one radiation source configured to transmit x-rays that intersect an object;
at least one detector configured to detect the x-rays;
a controller coupled to the detector; and
a computer configured to:
instruct the MECT system to detect components of plaque; and
generate a look-up table by using at least one phantom;
repeat the detection of the components of the plaque after instructing a user to administer a temperature-sensitive contrast agent to accentuate a visualization of the plaque.

15. An MECT system in accordance with claim 14, wherein the at least one phantom includes a simulated phantom, and to detect the components of the plaque, said computer is configured to:
produce the look-up table by using the simulated phantom, wherein the look-up table maps different densities of a selected basis material of the phantom to projection data for different energy spectra; and
obtain the components of the plaque by using the look-up table.

16. An MECT system in accordance with claim 15, wherein to generate the look-up table, said computer is configured to:
obtain first and second sets of density distribution images of the simulated phantom with a set of known material properties by:
simulating placement of the simulated phantom in a scanning field of the MECT system; and
simulating a scan of the simulated phantom at first and second energy levels using the MECT system.

17. An MECT system in accordance with claim 16, wherein to obtain the components of the plaque, said computer is configured to:
instruct the MECT system to place an object in the scanning field of the MECT system;
instruct the MECT system to scan the object at the first and second energy levels to obtain projection data of the object; and
determine, from the look-up table, densities of the object by reversely mapping the projection data of the object to the densities of the selected basis material, wherein the selected basis material includes at least one of iodine and water.

18. An MECT system in accordance with claim 14 wherein said computer is configured to:
instruct the MECT system to perform additional scans of the object at different times; and
repeat the detection of the components of the plaque.

19. An MECT system in accordance with claim 14 wherein said computer is configured to:
  instruct a user to administer a contrast agent in at least one of lipid-avid agents of the plaque, plaque specific antigens of the plaque, and plaque cells of the plaque; and
  repeat the detection of the components of the plaque.

20. An MECT system in accordance with claim 14 wherein said computer is configured to instruct the user to administer a the temperature-sensitive contrast agent in an inflamed plaque.

21. An MECT system in accordance with claim 14, wherein to quantify the components of the plaque, said computer is configured to:
  calculate composition distributions of the plaque; and
  calculate total plaque burden.

22. An MECT system in accordance with claim 14 wherein said computer is configured to:
  instruct a display device to display at least one of a 2-dimensional (2D) and a 3-dimensional (3D) image of the components of the plaque on a wall of an organ of the object; and
  enable viewing, from a viewpoint, a volume of the plaque in the 3D image.

23. An MECT system in accordance with claim 14, wherein said computer is configured to:
  improve quality of images of an object having at least one of metal stents and valves by removing beam-hardening artifacts in the images; and
  enable visualization of restenosis within at least one of the metal stents by repeating said detecting the components of plaque.

24. A computer readable medium encoded with a program configured to instruct a computer to detect components of plaque within an object that is scanned using a multi-energy tomography (MECT) system, the program further configured to instruct the computer to generate, by using at least one phantom, a look-up table that maps different densities of a selected basis material of the phantom to projection data for different energy spectra, and to repeat the detection of the components of the plaque after instructing a user to administer a contrast agent to accentuate a visualization of the plaque.

25. A computer encoded with a program configured to instruct an MECT system to detect components of plaque within an object that is scanned using the MECT system, the program further configured to instruct the computer to generate, by using at least one phantom, a look-up table that maps different densities of a selected basis material of the phantom to projection data for different energy spectra, and to quantify the components of the plaque by determining a weighted sum of densities, greater than a specific amount, of pixels of an image of an organ including the plaque.

* * * * *

UNITED STATES PATENT AND TRADEMARK OFFICE
CERTIFICATE OF CORRECTION

PATENT NO. : 7,031,426 B2
APPLICATION NO. : 10/625437
DATED : April 18, 2006
INVENTOR(S) : Iatrou et al.

It is certified that error appears in the above-identified patent and that said Letters Patent is hereby corrected as shown below:

On the Title Page, Item (54)
In Title, delete "SYSTEM" and insert therefor --SYSTEMS--.
In Claim 14, column 12, line 24, delete "plaque; and" and insert therefor --plaque;--.
In Claim 14, column 12, line 25, after "phantom;" insert --and--.
In Claim 20, column 13, line 10, delete "administer a the" and insert therefor --administer the--.

Signed and Sealed this

Twenty-fourth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,031,426 B2
APPLICATION NO. : 10/625437
DATED : April 18, 2006
INVENTOR(S) : Iatrou et al.

Page 1 of 1

It is certified that error appears in the above-identified patent and that said Letters Patent is hereby corrected as shown below:

On the Title Page, Item (54) and Column 1, line 1
In Title, delete "SYSTEM" and insert therefor --SYSTEMS--.
In Claim 14, column 12, line 24, delete "plaque; and" and insert therefor --plaque;--.
In Claim 14, column 12, line 25, after "phantom;" insert --and--.
In Claim 20, column 13, line 10, delete "administer a the" and insert therefor --administer the--.

This certificate supersedes the Certificate of Correction issued June 24, 2008.

Signed and Sealed this

Twenty-second Day of July, 2008

JON W. DUDAS
*Director of the United States Patent and Trademark Office*